US012735372B2

(12) United States Patent
Zellhuber et al.

(10) Patent No.: US 12,735,372 B2
(45) Date of Patent: Sep. 15, 2026

(54) PRODUCING ETHYLENE BY OXIDATIVELY DEHYDROGENATING ETHANE

(71) Applicant: LINDE GMBH, Pullach (DE)

(72) Inventors: Mathieu Zellhuber, Martinsried (DE); Martin Schubert, Munich (DE); Andreas Meiswinkel, Rimsting (DE)

(73) Assignee: LINDE GMBH, Pullach (DE)

( * ) Notice: Subject to any disclaimer, the term of this patent is extended or adjusted under 35 U.S.C. 154(b) by 391 days.

(21) Appl. No.: 18/548,887

(22) PCT Filed: Mar. 14, 2022

(86) PCT No.: PCT/EP2022/056565
§ 371 (c)(1),
(2) Date: Sep. 1, 2023

(87) PCT Pub. No.: WO2022/194790
PCT Pub. Date: Sep. 22, 2022

(65) Prior Publication Data
US 2024/0166579 A1 May 23, 2024

(30) Foreign Application Priority Data
Mar. 15, 2021 (EP) ..................................... 21162659

(51) Int. Cl.
*C07C 5/333* (2006.01)
*B01J 8/06* (2006.01)

(52) U.S. Cl.
CPC ................. *C07C 5/333* (2013.01); *B01J 8/06* (2013.01); *B01J 2208/00017* (2013.01)

(58) Field of Classification Search
CPC .... C07C 5/333; C07C 5/48; B01J 8/06; B01J 2208/00017; B01J 2208/00212;
(Continued)

(56) References Cited

U.S. PATENT DOCUMENTS 3,709,951 A 1/1973 Hutson et al.
5,066,365 A 11/1991 Roscher et al.
(Continued)

FOREIGN PATENT DOCUMENTS

CA 926622 A 5/1973
CA 3100928 A1 12/2019
(Continued)

OTHER PUBLICATIONS

International Search Report and Written Opinion issued in related App. No. PCT/EP2022/056565, mailed Jun. 9, 2022.
(Continued)

*Primary Examiner* — In Suk C Bullock
*Assistant Examiner* — Jason Y Chong
(74) *Attorney, Agent, or Firm* — AVEK IP, LLC

(57) ABSTRACT

A process for producing ethylene by oxidative dehydrogenation of ethane using a shell-and-tube reactor having reaction tubes extending between a first end and a second end includes disposing one or more catalyst beds in each of the reaction tubes. In each of the reaction tubes, a ratio of a total length of the one or more catalyst beds between the first end and the second end to a diameter of each of the reaction tubes has a value between 150 and 400. The shell-and-tube reactor is operated at a linear velocity of 250 to 800 cm/s, and the one or more catalyst beds are configured such that a ratio of active catalyst mass to effective cooling area is in a range between 1.5 and 5 $kg/m^2$.

19 Claims, 6 Drawing Sheets

(58) Field of Classification Search
CPC ...... B01J 2208/0053; B01J 2208/00548; B01J 2208/021; B01J 2208/025; B01J 2219/00033; B01J 19/30; Y02P 20/52
See application file for complete search history.

(56) References Cited

U.S. PATENT DOCUMENTS

| | | | |
|---|---|---|---|
| 5,820,747 | A | 10/1998 | Lenglet et al. |
| 5,907,056 | A | 5/1999 | Karim et al. |
| 6,030,920 | A | 2/2000 | Karim et al. |
| 6,237,341 | B1 | 5/2001 | Koike et al. |
| 6,258,992 | B1 | 7/2001 | Karim et al. |
| 8,519,210 | B2 | 8/2013 | Arnold et al. |
| 9,963,412 | B2 * | 5/2018 | Bos ........................ B01J 37/031 |
| 10,017,432 | B2 | 7/2018 | Bos et al. |
| 10,730,810 | B2 | 8/2020 | Peschel et al. |
| 10,730,811 | B2 | 8/2020 | Zellhuber et al. |
| 2002/0058849 | A1 | 5/2002 | Colling et al. |
| 2002/0082445 | A1 | 6/2002 | Ellis et al. |
| 2005/0148791 | A1 | 7/2005 | Lucy et al. |
| 2005/0261532 | A1 | 11/2005 | Stell et al. |
| 2008/0132723 | A1 | 6/2008 | Johnston et al. |
| 2010/0048972 | A1 | 2/2010 | Sun et al. |
| 2010/0256432 | A1 | 10/2010 | Arnold et al. |
| 2014/0024873 | A1 | 1/2014 | De Haan et al. |
| 2014/0066650 | A1 | 3/2014 | Aslam et al. |
| 2016/0304432 | A1 | 10/2016 | Bos et al. |
| 2019/0062236 | A1 | 2/2019 | Beauchamp et al. |
| 2019/0194091 | A1 | 6/2019 | Mitkidis et al. |
| 2019/0359544 | A1 | 11/2019 | Zellhuber et al. |
| 2020/0002251 | A1 | 1/2020 | Mitkidis et al. |
| 2023/0046854 | A1 | 2/2023 | Kaiser et al. |
| 2024/0150262 | A1 | 5/2024 | Zellhuber et al. |
| 2024/0166579 | A1 | 5/2024 | Zellhuber et al. |
| 2024/0317667 | A1 | 9/2024 | De Val et al. |
| 2025/0051665 | A1 | 2/2025 | Kracker et al. |
| 2025/0129303 | A1 | 4/2025 | Kracker et al. |

FOREIGN PATENT DOCUMENTS

| | | | |
|---|---|---|---|
| CN | 1063096 | A | 7/1992 |
| CN | 101360552 | A | 2/2009 |
| CN | 102905782 | A | 1/2013 |
| CN | 103086821 | A | 5/2013 |
| CN | 103086824 | A | 5/2013 |
| CN | 103086824 | B | 5/2013 |
| DE | 102011102971 | A1 | 12/2012 |
| DE | 102019119540 | A1 | 1/2021 |
| EP | 0100406 | A1 | 2/1984 |
| EP | 1140355 | B1 | 10/2001 |
| EP | 2096157 | A2 | 9/2009 |
| EP | 2740718 | A1 | 6/2014 |
| EP | 2772524 | A1 | 9/2014 |
| EP | 3249027 | A1 | 11/2017 |
| EP | 3339277 | A1 | 6/2018 |
| EP | 3456703 | A1 | 3/2019 |
| EP | 3519377 | B1 | 8/2019 |
| EP | 3558910 | B1 | 10/2019 |
| EP | 3708557 | A1 | 9/2020 |
| EP | 3708558 | A1 | 9/2020 |
| RU | 2730518 | C2 | 8/2020 |
| WO | 9301155 | A1 | 1/1993 |
| WO | 9805620 | A1 | 2/1998 |
| WO | 0069802 | A1 | 11/2000 |
| WO | 0190042 | A1 | 11/2001 |
| WO | 2010014153 | A2 | 2/2010 |
| WO | 2010115108 | A1 | 10/2010 |
| WO | 2011056597 | A2 | 5/2011 |
| WO | 2011097190 | A2 | 8/2011 |
| WO | 2013101373 | A1 | 7/2013 |
| WO | 2013122645 | A1 | 8/2013 |
| WO | 2014134703 | A1 | 9/2014 |
| WO | 2015181302 | A1 | 12/2015 |
| WO | 2017144584 | A1 | 8/2017 |
| WO | 2017198762 | A1 | 11/2017 |
| WO | 2018019760 | A1 | 2/2018 |
| WO | 2018019761 | A1 | 2/2018 |
| WO | 2018024650 | A1 | 2/2018 |
| WO | 2018082945 | A1 | 5/2018 |
| WO | 2018114747 | A1 | 6/2018 |
| WO | 2018114752 | A1 | 6/2018 |
| WO | 2018114900 | A1 | 6/2018 |
| WO | 2018115414 | A1 | 6/2018 |
| WO | 2018115416 | A1 | 6/2018 |
| WO | 2018115418 | A1 | 6/2018 |
| WO | 2018115494 | A1 | 6/2018 |
| WO | 2018153831 | A1 | 8/2018 |
| WO | 2019081682 | A1 | 5/2019 |
| WO | 2019175731 | A1 | 9/2019 |
| WO | 2019175732 | A1 | 9/2019 |
| WO | 2019243480 | A1 | 12/2019 |
| WO | 2020002326 | A1 | 1/2020 |
| WO | 2020074750 | A1 | 4/2020 |
| WO | 2020187572 | A1 | 9/2020 |
| WO | 2023049570 | A1 | 3/2023 |

OTHER PUBLICATIONS

Office Action issued May 14, 2026 in AE Application No. P6002319/2023, 6 pages.

* cited by examiner

PRODUCING ETHYLENE BY OXIDATIVELY DEHYDROGENATING ETHANE

CROSS-REFERENCE TO RELATED APPLICATIONS

This application is the national phase of, and claims priority to, International Application No. PCT/EP2022/056565, filed Mar. 14, 2022, which claims priority to European Patent Application No. EP 21162659.3, filed Mar. 15, 2021.

FIELD OF THE INVENTION

The invention relates to a process and a plant for the production of ethylene by oxidative dehydrogenation of ethane.

BACKGROUND

The oxidative dehydrogenation (ODH) of kerosenes with two to four carbon atoms is known in principle. In ODH, said kerosenes are reacted with oxygen to form, among other things, the respective olefins and water. The invention relates to the oxidative dehydrogenation of ethane to ethylene, hereinafter also referred to as ODHE.

ODH can be advantageous over more established olefin production processes such as steam cracking or catalytic dehydrogenation. For example, there is no thermodynamic equilibrium limitation due to the exothermy of the reactions involved and the practically irreversible formation of water. ODH can be carried out at comparatively low reaction temperatures. In principle, no regeneration of the catalysts used is required, since the presence of oxygen enables or causes in situ regeneration. Finally, in contrast to steam cracking, smaller amounts of worthless by-products such as coke are formed.

For further details regarding ODH, reference is made to relevant literature, for example Ivars, F. and López Nieto, J. M., Light Alkanes Oxidation: Targets Reached and Current Challenges, in Duprez, D. and Cavani, F. (eds.), Handbook of Advanced Methods and Processes in Oxidation Catalysis: From Laboratory to Industry, London 2014: Imperial College Press, pages 767-834, or Gärtner, C. A. et al, Oxidative Dehydrogenation of Ethane: Common Principles and Mechanistic Aspects, ChemCatChem, vol. 5, no. 11, 2013, pages 3196 to 3217, and X. Li, E. Iglesia, Kinetics and Mechanism of Ethane Oxidation to Acetic Acid on Catalysts Based on Mo—V—Nb Oxides, J. Phys. Chem. C, 2008, 112, 15001-15008.

In ODH, significant amounts of the respective carboxylic acids of the kerosenes used, in particular acetic acid in the case of ODHE, are formed as by-products under industrially relevant reaction conditions, especially when catalysts based on $MoVNbO_x$ and $MoVNbTeO_x$ are used. For economical plant operation, therefore, a co-production of olefins and the carboxylic acids is generally unavoidable when using the catalyst type described.

Due to the formation of acetic acid, the possible applications of ODHE are limited by the not always given utilization possibilities of this co-product, whereas for ethylene often significantly larger quantities would be desirable. Only in individual cases is it possible to link ODHE directly to processes that require ethylene and acetic acid at the same time, e.g. in vinyl acetate monomer (VAM) production, as described in WO 2018/114747 A1 and WO 2018/114752 A1, among others. However, such approaches also involve only utilization of acetic acid and not a solution to the problem of co-production.

Although WO 2018/115416 A1 already describes a possibility to adjust the product ratio between ethylene and acetic acid in ODHE within certain limits as required by adjusting the water partial pressure in the product gas, a significant amount of acetic acid continues to be produced even with an appropriate adjustment.

WO 2018/114900 A1 describes reactor geometries for a tubular reactor, claiming in particular tube geometries with a length of 4 to 12 m and a diameter of 15 to 25 mm. Different catalyst geometries are also disclosed. Catalysts based on $MoVNbO_x$ are used and $MoVNbTeO_x$ catalysts are also explicitly mentioned as an option. However, no reference is found to the effect of parameter changes such as increased linear velocities on the product distribution. The background of WO 2018/114900 A1 is a reactor system that enables sufficiently isothermal reaction control with minimized pressure loss. Against this background, this document states that particularly high linear velocities tend to be disadvantageous, since they cause an increased pressure loss, which is particularly detrimental in low-pressure processes such as ODHE. Therefore, in another document, U.S. Pat. No. 9,963,412 B2 or WO 2015/082598 A1, the linear velocity is limited to 500 cm/s as claimed.

WO 2020/074750 A1 contains details of pilot tests in a single-tube reactor on an industrial scale with a diameter of 19 mm and a length of 5.6 m. The subject matter disclosed in this document relate to the composition of the inert fraction in the process gas. No information is given on the linear velocity; furthermore, in all three experiments carried out, the conditions are hardly varied except for the inert composition and the reactor temperature.

WO 2017/144584 A1 discloses processes and associated reaction systems for the oxidative dehydrogenation of an alkane having 2 to 6 carbon atoms, preferably ethane or propane, more preferably ethane. In particular, a process is provided comprising supplying a feed gas comprising the alkane and oxygen to a reactor vessel comprising an upstream and downstream catalyst bed. Further, there is a contacting the feed gas with an oxidative dehydrogenation catalyst in the upstream catalyst bed, followed by contacting the feed gas with an oxidative dehydrogenation/oxygenation catalyst in the downstream catalyst bed to obtain a reactor effluent comprising the alkene. A supply of an upstream coolant to an upstream shell space of the reactor vessel from an upstream coolant loop and a downstream coolant to a downstream shell space of the reactor vessel from a downstream coolant loop is provided.

US 2016/304432 A1 relates to a process for the oxidative dehydrogenation of an alkane containing 2 to 6 carbon atoms and/or for the oxidation of an alkene containing 2 to 6 carbon atoms, wherein a gas stream containing oxygen and the alkane and/or alkene is contacted with a mixed metal oxide catalyst containing molybdenum, vanadium, niobium and optionally tellurium, and wherein the linear velocity of the gas stream is at least 10 cm/s.

From WO 93/01155 A1 a process for the production of maleic anhydride by catalytic oxidation of a non-aromatic hydrocarbon having at least four carbon atoms in a straight chain is known, in which a gas containing oxygen and hydrocarbon is passed through a fixed catalyst bed in a tubular reactor. The activity of the catalyst bed is graded.

In summary, it can be stated that known optimizations of the catalyst and process optimizations to date only lead to an improvement in ethylene yield to a limited extent. Further measures are therefore desirable which go beyond the state of the art, which up to now has only allowed the co-products to be adapted as required within certain limits or the use of both products in downstream processes.

SUMMARY

The invention thus has an object of providing a reactor setup and operating conditions that enable maximum ODH-E process intensification to be achieved under large-scale conditions, in particular with a focus on optimized ethylene yield.

According to one embodiment of the invention, a method for producing ethylene by oxidative dehydrogenation of ethane includes using a shell-and-tube reactor having reaction tubes extending between a first end and a second end. A plurality of catalyst beds are disposed in each of the reaction tubes, and in each of the reaction tubes, a ratio of a total length of the plurality of catalyst beds between the first end and the second end to a diameter of each of said reaction tubes has a value between 150 and 400. The shell-and-tube reactor is operated at a linear velocity of 250 to 800 cm/s. The plurality of catalyst beds are configured such that the plurality of catalyst beds in each of the reaction tubes have a different catalyst activity. An average ratio of active catalyst mass to effective cooling surface for the plurality of catalyst beds in each of the reaction tubes is in a range between 1.5 and 5 kg/m$^2$, wherein in at least one of the catalyst beds in each of the reaction tubes considered individually, a ratio of active catalyst mass to effective cooling surface is in this range.

According to another embodiment, a plant for producing ethylene by oxidative dehydrogenation of ethane includes a shell-and-tube reactor having reaction tubes extending between a first end and a second end. A plurality of catalyst beds are disposed in each of the reaction tubes. In each of the reaction tubes, a ratio of a total length of the plurality of catalyst beds between the first end and the second end to a diameter of each of the reaction tubes has a value between 150 and 400. The shell-and-tube reactor is configured to operate at a linear velocity of 250 to 800 cm/s. A plurality of catalyst beds are configured such that the plurality of catalyst beds in each of the reaction tubes have a different catalyst activity. An average ratio of active catalyst mass to effective cooling area for the plurality of catalyst beds in each of the reaction tubes is in a range between 1.5 and 5 kg/m$^2$, wherein in at least one of the catalyst beds in each of the reaction tubes considered individually, a ratio of active catalyst mass to effective cooling surface is in this range.

WRITTEN DESCRIPTION

Figure 1:
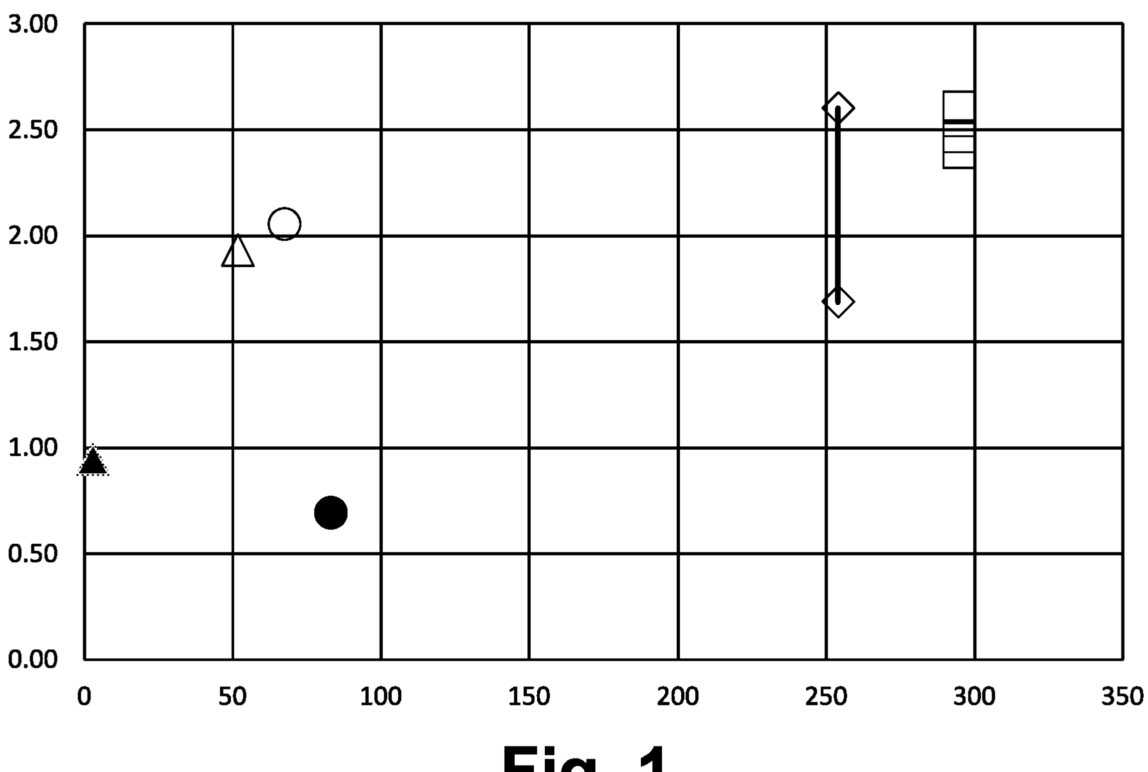
FIGS. 1 to 9 illustrate data determined according to the invention and comparative data not according to the invention in the form of diagrams.

Before explaining the features and advantages of the invention, other fundamentals of the invention are first explained and terms used in describing the invention are introduced.

As is customary in the art, catalyst mass is understood here to mean the mass of active catalyst material expressed, for example, in kg (i.e. without inert particles or support materials and/or inert binder components), see also the explanations below relating to the catalyst beds used.

The weight hourly space velocity (WHSV) is the quantity of gas (containing the reactants to be reacted, including possible inert gas additives), expressed in kg, which is passed over a quantity of catalyst, expressed in kg, in one hour. Thus, the WHSV is equal to the quotient of the mass flow rate (in kg/h) and the mass of the active catalyst (in kg) or kg gas/(kg catalyst× h). This definition corresponds to the convention used in WO 2015/082602 A1.

Linear velocity is defined as the speed of a gas flow (in cm/s) through a reactor or reaction tube in the axial direction or along a flow path, taking into account the amount of empty space in the catalyst bed available for the flow. The linear velocity in m/h is thus calculated from the gas volume flow rate at the beginning of the active catalyst bed (in m$^3$/h), divided by the internal cross-sectional area of the reaction tube (in m$^2$) and additionally by the average void fraction in the catalyst bed (dimensionless). This definition corresponds to the convention used in WO 2015/082598 A1. The linear velocity is converted from the unit m/h to the unit cm/s used for numerical data in this application by means of the usual mathematical conversion.

The term shell-and-tube reactor describes a chemical reactor in which an exothermic reaction (in this case oxidative dehydrogenation) is carried out in the gas phase. The gas mixture to be reacted is converted with the aid of a catalyst in several fluidically parallel-connected and typically straight and, in particular, upright tubes, around which one or more cooling media, in particular a molten salt, flow in an outer vessel (shell).

The term catalyst bed is used herein to mean a bed or solid structure comprising a catalyst material and optionally an inert material as a support or binder. Furthermore, at least parts of a catalyst bed may optionally also contain inert bulk particles. If there is talk of several catalyst beds, these can be arranged one behind the other in the flow direction without or with intermediate zones, in particular inert zones without catalyst material. In general, the flow direction of a gas with the reactants to be reacted corresponds in the present case to the axial direction of the reaction tubes.

In the following, there are several references to a ratio of a total length of a plurality of catalyst beds between the ends of one or more reaction tubes to a diameter of each of the reaction tubes, also referred to as "total length-to-diameter ratio" for short. Here, the total length of the plurality of catalyst beds between the ends of the one or more reaction tubes is understood to be the length occupied by the plurality of (active) catalyst beds in a single reaction tube or each reaction tube. This corresponds at most to the total length of the respective reaction tube between its ends if no catalyst-free areas are present. For the above value, (only) those areas are always considered in which an active catalyst material is provided in a mass fraction of more than 1, 2 or 5%. In case of several catalyst beds or catalyst layers, their lengths are summed up. The length or total length of the reaction tubes is equal to the height or total height of the reaction tubes in a typically used upright shell-and-tube reactor. The diameter is understood to be the inner diameter of the respective reaction tube under consideration.

The effective or efficient cooling surface of one or more reaction tubes (the terms "effective" and "efficient" are used synonymously in this context) is referred to here as the sum of all reactor tube inner surfaces surrounding catalytically active layers (with the minimum mass fractions of active catalyst material just mentioned) in the one or more reaction tubes, respectively. Reactor tube inner surfaces surrounding inert layers or empty reactor tube sections are thus not included here. In this context, the effective or efficient cooling surface of a single catalyst bed is to be understood in the linguistic usage used here as the inner surface of the reaction tube or reactor tube inner surface surrounding this active layer. As there is a plurality of catalyst beds, the effective or efficient cooling surface for these catalyst beds is the sum of the inner surfaces of the reaction tube surrounding these multiple catalyst beds. These may be contiguous or interrupted, the latter being particularly the case if the catalytically active catalyst beds are interrupted by inert beds, empty tube sections, etc.

The "active catalyst mass" can in particular be the entire catalyst mass in a corresponding catalyst bed. If intentional or unintentional uneven distributions of the catalyst mass are present in this catalyst bed, this does not matter insofar as the entire active catalyst mass is considered here in particular.

The ratio of active catalyst mass to effective cooling surface can be defined as a single value for a single catalyst bed or for a reaction tube with only one catalyst bed. In this case, it is the quotient of the two quantities related to the catalyst bed or reaction tube under consideration and determined on the basis of the previously given definitions, i.e. the active catalyst mass in the catalyst bed and its effective cooling surface.

In the case of one or more reaction tubes with multiple catalyst beds, an average ratio of active catalyst mass to effective cooling surface may further be considered for this one or these multiple tubes. In particular, this average ratio is calculated by taking the quotient between the sum of the active catalyst masses of all catalytically active beds in the one or more reaction tubes and the sum of all reactor tube internal surfaces surrounding these catalytically active beds in the one or more reaction tubes.

As also explained below with reference to specific examples, the area-specific ethylene yield can be used as a measure of the process intensity of a process carried out in a shell-and-tube reactor for the production of ethylene by oxidative dehydrogenation of ethane, by which shall be understood here the ethylene yield per effective cooling surface (see immediately before). In particular, the specific ethylene yield is expressed in kg ethylene per hour per square meter of effective cooling surface with the unit kg/(h×m$^2$). This measure is particularly meaningful because the total cooling surface provided in the reactor is decisive for the construction effort and thus the investment costs of the reactor. With a higher area-specific ethylene yield, i.e. a higher process intensity in the sense understood here, a higher production output can be achieved with the same installed cooling surface, which leads to a desired process intensification and has a positive effect on the economic efficiency of the production plant. The term process intensification is used to describe the increase in process intensity.

Surprisingly, it has been recognized in the context of the invention that for large-scale reactors, under certain conditions, a significant process intensification can be achieved over the prior art while maintaining high stability and safety of the process control.

The examples given in the mentioned U.S. Pat. No. 9,963,412 B2 show values of less than 100 cm/s for the linear velocity. The accompanying formation of acetic acid is not mentioned. Thus, the aforementioned document does not allow any conclusions to be drawn regarding the speed ranges that are particularly advantageous for ethylene/acetic acid co-production. In addition, no conclusions can be drawn from the laboratory-scale examples mentioned in this publication as to preferred speed ranges for reactors on a commercial scale. The same applies, e.g., to U.S. Pat. No. 10,017,432 B2, in which preferred ranges of weight-related hourly space velocities are only given on the basis of laboratory tests.

In fact, laboratory reactors differ significantly from reactors used in large-scale plants, especially with respect to the aforementioned overall length-to-diameter ratio of the one reaction zone or multiple reaction zones. In this regard, the examples shown in the writings just cited have ratios of less than 100. However, within the scope of the invention, reactors with the aforementioned overall length-to-diameter ratios of the one reaction zone or the multiple reaction zones relevant for large-scale applications are considered.

As also explained below with reference to the figures, in which data partly determined from the prior art are contrasted with data according to the invention, processes proposed in the prior art and examples given there lead to specific ethylene yields (see above) of about 2 kg/(h×m$^2$) at the comparatively low overall length-to-diameter ratios of less than 100 mentioned.

A similar degree of process intensification can also be achieved for industrial-scale reactors and overall length-to-diameter ratios of the one reaction zone or the multiple reaction zones of 200 to 300, as also disclosed, for example, in WO 2018/115416 A1 and substantiated there with experimental results. The same applies to pilot tests in the prior art. In WO 2018/115416 A1, it was also shown in this context that an increase in the specific ethylene yield to values of about 2.5 kg/(h×m$^2$) could be achieved by increasing the flow rate and corresponding temperature adjustment. However, it can be seen that the increase achieved in this process is relatively flat, since at higher flow rates the maximum ethane conversion must be reduced, because otherwise a runaway of the reactor cannot be avoided. Due to this thermal limitation, a further increase of the ethane load would therefore lead to a relatively smaller and smaller increase of the process intensity.

In WO 2019/243480 A1, it was shown that by using a three-layer catalyst bed, a significant process intensification can be achieved compared to a single-layer catalyst bed. Here, too, values of up to 2.5 kg/(h×m$^2$) are achieved for the specific ethylene yield. Again, reference is made to the explanations of the figures for further details.

An evaluation of the data from the above-mentioned publications shows overall that the linear velocities required for similar ethylene yields are significantly higher for large-scale reactors than for laboratory reactors.

The values given in U.S. Pat. No. 9,963,412 B2, for example, are therefore not suitable for direct transfer to large-scale reactors. It is also shown that, in a comparison between a single-layer and a three-layer catalyst bed, an equivalent or better process intensity can be achieved at a lower linear velocity. The design of the catalyst bed is thus of great relevance, especially on an industrial scale.

Something similar to the linear velocity applies to the weight-related hourly space velocity, as also explained in more detail with reference to the figures, since the same level of process intensity can be achieved in large-scale reactors at significantly lower weight-related hourly space velocities than in the laboratory. Incidentally, a comparison of the data from U.S. Pat. No. 10,017,432 B2 and U.S. Pat. No. 9,963,412 B2 also shows that no clear relationship can be established between the weight-related hourly space velocity and the achievable process intensity.

The invention as a whole is directed to a process for producing ethylene by oxidative dehydrogenation of ethane using a shell-and-tube reactor having reaction tubes extending between a first end and a second end, wherein a plurality of catalyst beds are disposed in each of the reaction tubes, and a ratio of a total length of the plurality of catalyst beds between the first end and the second end to a diameter of each of the reaction tubes (i.e., said total length-to-diameter ratio of the reaction zone or reaction zones) in each of the reaction tubes has a value between 150 and 400, in particular between 200 and 280. Thus, the invention expressly relates to tube bundle reactors on a scale relevant to large-scale industrial applications. Where reference is made herein to "the reaction tubes", this may also refer to a subset of the total reaction tubes present. In other words, the statement that "each of the reaction tubes" is designed in a certain way may also mean that each of the reaction tubes of such a subset may be designed accordingly, but not all reaction tubes need to be designed in this way.

In accordance with the invention, the shell-and-tube reactor is operated at a linear velocity of 250, 300, 400 or 500 cm/s to 800 cm/s and the plurality of catalyst beds are further configured such that an average ratio of active catalyst mass to effective cooling surface for the plurality of catalyst beds in each of the reaction tubes is in a range between 1.5 and 5 $kg/m^2$, in particular between 2 and 4 $kg/m^2$. In other words, in the invention, a plurality of reaction tubes is provided, wherein each reaction tube has more than one catalyst bed and all catalyst beds are surrounded by an inner surface of the respective reaction tube. Herein, the ratio of the active catalyst mass of all catalyst beds in a reaction tube in sum to the summed inner surface area of the reaction tube surrounding all considered catalyst beds in that tube is in the range of 1.5 to 5 $kg/m^2$.

For example, in embodiments of the invention, if there are n reaction tubes (which may be a subset of a total number of m reaction tubes in the reactor as a whole), each of these n reaction tubes may have x catalyst beds, each of the x catalyst beds being surrounded by y inner surfaces of the reaction tube of the n reaction tubes in which the x catalyst beds are received. In this case, n and x may independently be integers of more than one, where y equals x. The summed active catalyst mass of all x catalyst beds divided by the sum of the y inner surfaces then gives the average ratio (when x is greater than one).

Thus, according to the invention, in a reaction tube having more than one catalyst bed of different activity and/or composition, it is possible in embodiments of the invention for the ratio of active catalyst mass to effective cooling surface, calculated separately for the individual beds, to be outside the above range between 1.5 and 5 $kg/m^2$, in particular between 2 and 4 $kg/m^2$, but for the average ratio for the reaction tube to be within said range.

In embodiments of the invention, as already expressed in other words, the average ratio of the active catalyst mass to the effective cooling surface at the plurality of catalyst beds in each of the reaction tubes is a quotient between a sum of the active catalyst masses in all of the respective catalyst beds and the sum of all inner surfaces of the reaction tube surrounding these catalyst beds, respectively.

According to the invention, a shell-and-tube reactor having a plurality of reaction tubes is used, wherein a plurality of catalyst beds are provided in each of the reaction tubes. In addition to the average ratio of active catalyst mass to effective cooling surface within the limits mentioned above and explained below (and corresponding embodiments), it is also provided that in each case at least one of the catalyst beds, considered separately, also has a ratio of active catalyst mass to effective cooling surface (for this bed) in this range, i.e. in particular in the range 1.5 to 5 $kg/m^2$.

Preferably, the shell-and-tube reactor used according to the invention is a shell-and-tube reactor with fixed catalyst beds in each individual reaction tube. In order to achieve overall economy as well as increased operational reliability, the individual reaction tubes are thereby equipped with several catalyst beds, in particular with 1, 2, 3, 4, 5 catalyst beds of, according to the invention, different activity and/or composition. The cooling or heating is carried out with a suitable cooling medium, in particular a thermal oil or preferably a molten salt, whereby this is conducted in co-current or counter-current to the direction of flow of the reaction feed, preferably in counter-current.

Different reaction zones can be achieved, on the one hand, by differently active catalyst layers (with increasing activity in the direction of flow of the reaction feed stream) and/or with differently cooled zones, i.e. different coolant or molten salt circuits (these in each case, if necessary, differently in co-current or counter-current). For example, the reactor can be designed as indicated in WO 2019/243480 A1.

Typical operating conditions are given, for example, in WO 2018/115416A1 and WO 2018/115418 A1 and in Tables 1A and 1B below.

The advantageous combination of reaction conditions and structural designs proposed according to the invention describes for the first time for reactors operated on a large scale a combination of design variables, namely the aspect ratio of the catalyst bed and the ratio of the catalyst mass to the cooling surface, and operating parameters, namely in particular the linear velocity, which enable a significant increase in process intensity in the oxidative dehydrogenation of ethane. According to the invention, it was recognized that significant improvement in terms of process intensification is only possible in a very specific range spanned by several parameters.

As shown below with reference to the figures (see in particular FIGS. 5 and 6 and associated explanations), a strong process intensification is achieved only for the claimed middle range of the ratio of catalyst mass to cooling surface by increasing the linear velocity. By contrast, under the conditions selected in the prior art with a high specific catalyst loading per cooling surface, there is no potential for further yield increases.

What is particularly surprising is the fact that in designs according to the invention, no thermal runaway is to be expected even for very high specific ethylene yields. For all considerations based on a tube diameter of 20 mm, an ethane conversion of more than 50% is always achieved, with a maximum temperature rise in the hotspot, i.e. the warmest point in the respective reaction tube, of less than 45 K, relative to an outlet temperature of the coolant used, here in particular a molten salt.

A reactor with a tube diameter of 26 mm generally results in higher temperature rises in the catalyst bed, which could also lead to thermal runaway at the point with the highest reactor load if the temperature of the coolant is increased further. It can thus be seen that only through a suitable catalyst bed design, with moderate ratios of catalyst mass to cooling surface, can the potential of increasing the linear velocity be exploited to a sufficient extent.

The effect of the reaction control according to the invention can be vividly described on the basis of the influences explained below.

With a higher linear velocity, the ODHE reactor can be operated at a higher reaction temperature, but still at moderate temperatures of 450 to 500° C. max. The higher reaction temperature is decisive for an increase in conversion with simultaneously increased ethylene selectivity. On the one hand, this leads to steep increases in the specific ethylene yield with increasing feed load (see in particular FIG. 9 and associated explanations). Without being too bound by theory, an explanation of this is given in WO 2019/243480 A1. This effect could also be reproduced in the context of the invention.

At moderate average catalyst loading per cooling surface, the removal of heat is favored, especially in the hotspot region, so that a higher stability of the reaction with respect to thermal runaway is achieved. However, at large-scale production rates, the ratio must exceed a minimum of 1.5, preferably 2, to ensure economical operation.

A high linear velocity can preferably be achieved by increasing the total volume flow with unchanged composition at the catalyst bed inlet or, in particular, by selecting a reaction tube with the smallest possible diameter. The latter, however, must still be large enough to allow a sufficiently large quantity of commercial catalyst bodies to be packed into the reaction tube or across the tube cross-section in order to keep the proportion of bypass flow as low as possible and catalyst utilization as high as possible.

Too small a tube cross-section would mean that the effective diameter of the catalyst bodies would also have to be significantly reduced, resulting in an unacceptably high pressure drop across the respective tube.

If the tube cross-section is too large, the gas load and thus the catalyst load would have to be increased too much to achieve a high linear velocity in order to keep the ethane conversion within an economically reasonable range. This is associated with a very strong heat tone of the reaction and also a lower heat dissipation from the tube into the cooling medium of the reactor due to a large tube cross-section. This would increase the risk of thermal runaway. Therefore, a cooled tube bundle reactor is used, with the inner diameter of the individual tube preferably being 10 to 32 mm, in particular 12 to 26 mm, especially 15 to 21 mm.

If necessary, an increase in the linear velocity can also be achieved by increasing the total feed gas flow while changing the composition at the start of the catalyst bed. In order to avoid excessive heat toning of the reaction, the increase in gas load can be achieved in particular by dilution with an inert gas. A gas or a gas mixture from the group of noble gases (i.e. He, Ne, Ar, Kr or Xe), carbon dioxide, nitrogen or methane can be used as the inert gas in this case. However, carbon dioxide, nitrogen or methane are particularly suitable for a technical process. In particular, a high linear velocity can be achieved by combining reactant gas dilution and the use of the smallest possible reaction tube cross-section. A further increase in the water (vapor) content in the reactant gas beyond that required for catalyst stability, as described in WO 2018/115418 A1, should be avoided here in order to maintain the selectivity advantage to ethylene that can be achieved according to the invention.

The invention significantly enhances the economic benefits of ODHE technology, since the reactors can be built much smaller (in terms of the number and length of the individual tubes of a shell-and-tube reactor, see Tables 1A and 1B) and with a reduced heat exchange surface for the same plant capacity in terms of ethylene product, which results in higher process intensity. Furthermore, a technical implementation for larger plant capacities (in terms of ethylene product) is also facilitated.

In a particularly advantageous embodiment of the invention, the shell-and-tube reactor is operated with a weight-related hourly space velocity of more than 3 or 5 kg and less than 20 kg feed per hour and kg catalyst. The specific advantages of this mode of operation and of the aspects thereof also indicated below arise in particular in combination with the further features according to the invention and provided in accordance with advantageous embodiments, and are also explained below with reference to the accompanying figures.

According to the invention, the linear velocity used in the shell-and-tube reactor is advantageously more than 250, 300, 400 or 500 cm/s, but less than 800 cm/s.

Advantageously, the shell-and-tube reactor is operated such that a maximum temperature in the plurality of catalyst beds is less than 500 or 450° C.

In the shell-and-tube reactor, the plurality of catalyst beds advantageously use packing selected from rings, in particular Raschig rings, pellets, in particular cylindrical pellets, and extrudates or combinations thereof. In particular, the extrudates can have a high surface area, which can be achieved by appropriate geometric shapes such as so-called cloverleaf structures.

In the process according to the invention, several catalyst beds with different catalyst activity are used, as for example disclosed in WO 2019/243480 A1 and already mentioned above.

A particularly advantageous embodiment of the invention comprises metering a water (vapor) addition into the feed stream to the shell-and-tube reactor, hereinafter also referred to as water feed, as a function of a detected catalyst activity in the shell-and-tube reactor, for example determined via a measured temperature, as also disclosed in WO 2018/115418 A1. A metering of the water feed can also be used to control the product ratio between ethylene and acetic acid, as disclosed in WO 2018/115416 A1, in particular as a function of the determined water partial pressure in the product gas at the reactor outlet.

A method according to a particularly preferred embodiment of the invention comprises flowing one or more cooling media through the shell-and-tube reactor, thereby cooling different regions of the shell-and-tube reactor, in particular to different extents.

A plant for producing ethylene by oxidative dehydrogenation of ethane, comprising a shell-and-tube reactor having reaction tubes extending between a first end and a second end is also an object of the invention. A plurality of catalyst beds are disposed in each of the reaction tubes, and a ratio of a total length of the plurality of catalyst beds between the first end and the second end to a diameter of each of the reaction tubes in each of the reaction tubes has a value between 150 and 400. According to the invention, the shell-and-tube reactor of the apparatus of the invention is arranged to operate at a linear velocity of 250 to 800 cm/s, and the plurality of catalyst beds are arranged such that an average ratio of active catalyst mass to effective cooling surface is in a range between 1.5 and 5 $kg/m^2$. In at least one of the catalyst beds in each of the reaction tubes considered individually, a ratio of active catalyst mass to effective cooling surface is in this range. The plurality of catalyst beds in each of the reaction tubes have a different catalyst activity.

With regard to the plant provided according to the invention and its features, reference is expressly made to the above explanations concerning the process according to the invention, since these concern a corresponding plant in the same way. The same applies in particular to an embodiment of a corresponding plant which is advantageously set up for carrying out a corresponding process in any embodiment.

One embodiment of the process according to the invention comprises that the oxidative dehydrogenation is carried out at a temperature of the catalyst in a range between 240 and 500° C., preferably between 280 and 450° C.

In a further embodiment, one or more reactors are used for the oxidative dehydrogenation and the total pressure of the reaction feed stream at the inlet of the reactor(s) is selected in a range between 1 and 10 bar (abs.), preferably between 2 and 7 bar (abs.).

The advantageously used water content of the reaction feed stream is in a range between 5 and 95 vol %, in particular 10 and 50 vol %, especially 14 and 35 vol %. The molar ratio of water to ethane in the reaction feed stream can be at least 0.23.

The catalyst used may contain at least the elements molybdenum, vanadium, niobium and optionally tellurium, in particular in the form of a mixed oxide.

The invention is further explained below with reference to specific examples according to the invention and comparative examples with associated figures, as well as to a figure illustrating one embodiment of the invention.

FIGS. 1 to 9 illustrate data obtained according to the invention and comparative data not according to the invention in the form of diagrams.

As mentioned, prior art laboratory reactors, such as those used according to U.S. Pat. No. 10,017,432 B2 and U.S. Pat. No. 9,963,412 B2, have side ratios of less than 100. However, in the context of the invention, the focus is on reactors with a side ratio between 150 and 400, which is particularly relevant for large-scale applications.

FIG. 1 illustrates data computationally determined on the basis of the disclosure of the repeatedly mentioned U.S. Pat. No. 10,017,432 B2 (hereinafter referred to as publication 1), and further data determined on the basis of the disclosure of the repeatedly mentioned U.S. Pat. No. 9,963,412 B2 (publication 2). Furthermore, data determined on the basis of the mentioned WO 2020/074750 A1 (publication 3) are shown. Data according to publication 1 are shown in the form of circles, where filled circles denote data from comparative examples. Data according to publication 2 are illustrated in the form of triangles, with filled triangles denoting data from comparative examples. Squares lying on an edge correspond to data according to publication 3 or the pilot plant disclosed therein. Data determined on the basis of WO 2018/115416 A1 (publication 4) are shown as diamonds or oblique squares and are connected with a line.

The diagram in FIG. 1 and all subsequent diagrams indicate on the vertical axis as a measure of process intensification the specific ethylene yield mentioned several times above, i.e. the ethylene yield per effective cooling surface in kg/(h×m$^2$). On the horizontal axis, FIG. 1 shows the total length/diameter ratio in dimensionless units.

FIG. 1 shows that the positive examples from the laboratory-based data in the above-mentioned publications 1 and 2 (unfilled circles and triangles) lead to specific ethylene yields of about 2 kg/(h×m$^2$) at small length-diameter ratios of less than 100.

An only slightly higher level of process intensity with specific ethylene yields of about 2.5 kg/(h×m$^2$) can also be achieved for industrial-scale reactors and aspect ratios of 200 to 300, as also evidenced, for example, from the data in Publication 4 (slanted squares) and Publication 3 (horizontal squares).

Figure 2:
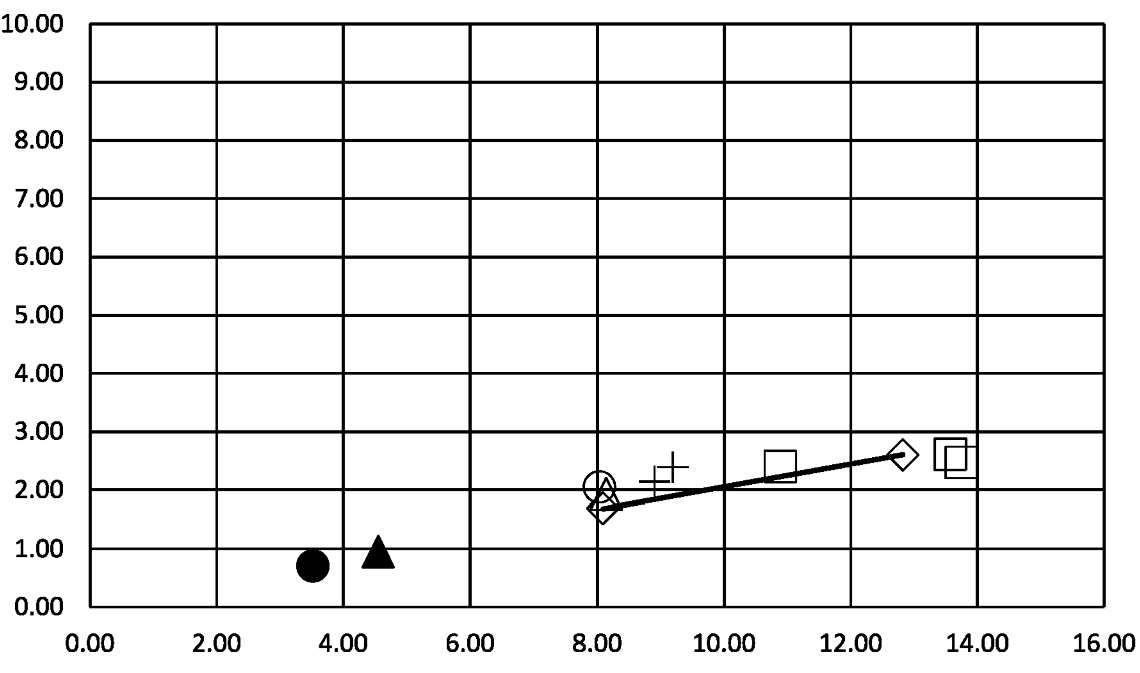

In addition to the data already explained for FIG. 1, FIG. 2 also illustrates data obtained in accordance with WO 2019/243480 A1 (publication 5) assuming different reaction tube diameters. The data are illustrated in the form of vertical crosses, where the data point at the bottom left corresponds to a reaction tube diameter of 26 mm, and the data point at the top right corresponds to a reaction tube diameter of 20 mm. In publication 5, it was shown that by using a three-layer catalyst bed, a significant process intensification can be achieved compared to a single-layer bed. The corresponding data points were determined under these conditions. The vertical axis corresponds to the vertical axis shown in FIG. 1. On the horizontal axis, the loading with feed per cooling surface is given in kg/(h×m$^2$), i.e. the quotient between feed gas mass flow and effective cooling surface.

As can also be seen from the data according to publication 4 (oblique squares), an increase in the specific ethylene yield to the above-mentioned values of approx. 2.5 kg/(h & m$^2$) can be achieved by increasing the flow rate and adjusting the temperature accordingly. Also according to publication 5 (vertical crosses), values of up to 2.5 kg/(h×m$^2$) can be achieved for the specific ethylene yield. However, it can be seen in particular that the increase achieved in this case is relatively flat, since at higher flow rates (test point 56 according to publication 4) the maximum ethane conversion was lower, since otherwise a runaway of the reactor could not be avoided. Due to this limitation, a further increase in the ethane load would therefore lead to a relatively smaller and smaller increase in the process intensification.

Figures 3, 4:
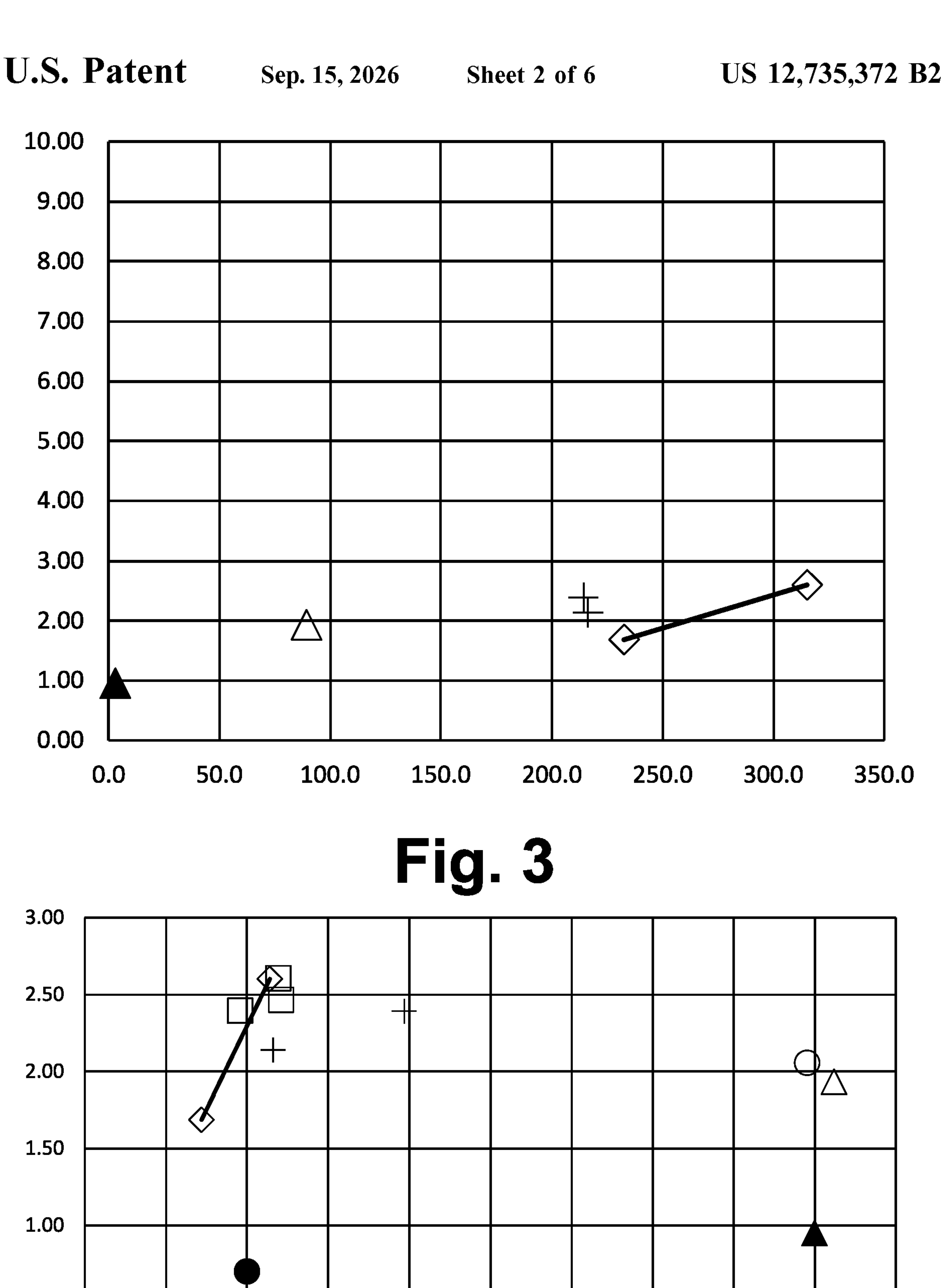

FIG. 3 illustrates part of the data already explained for FIG. 2, where the linear velocity is indicated in cm/s on the horizontal axis. The data according to publication 5 are again illustrated with crosses, whereby the data point at the top left corresponds to a reaction tube diameter of 20 mm, and the data point at the bottom right corresponds to a reaction tube diameter of 26 mm.

As can be seen from FIG. 3, the linear velocities required for similar ethylene yields are significantly higher for large-scale reactors than for laboratory reactors. The definition given in publication 2 was used to determine the linear velocity. The values given in publication 2 are not suitable for direct transfer to large-scale reactors. It is also shown that in the comparison of single- to triple-layer beds (vertical crosses according to publication 5), an equivalent or better process intensity can be achieved at a lower linear velocity. The design of the catalyst bed is thus of great relevance, as already explained, particularly on an industrial scale.

FIG. 4 illustrates the data already explained for FIGS. 2 and 3, with the WHSV indicated on the horizontal axis in kg gas/(kg catalyst× h). The data according to publication 5 are again illustrated with crosses, where the data point at the bottom left corresponds to a reaction tube diameter of 26 mm, and the data point at the top right corresponds to a reaction tube diameter of 20 mm.

FIG. 4 shows that a distinction between laboratory and large-scale reactors as for the linear velocity according to FIG. 3 also applies to the WHSV, since the same level of process intensity can be achieved in large-scale reactors at significantly lower WHSV than in the laboratory. Furthermore, a comparison of the data from publications 1 and 2 (circles and triangles) also shows that no clear relationship can be established between WHSV and achievable process intensity.

The invention now permits further process intensification in embodiments according to the invention for large-scale reactors, with the greatest possible stability and safety of the process control.

Figure 5:
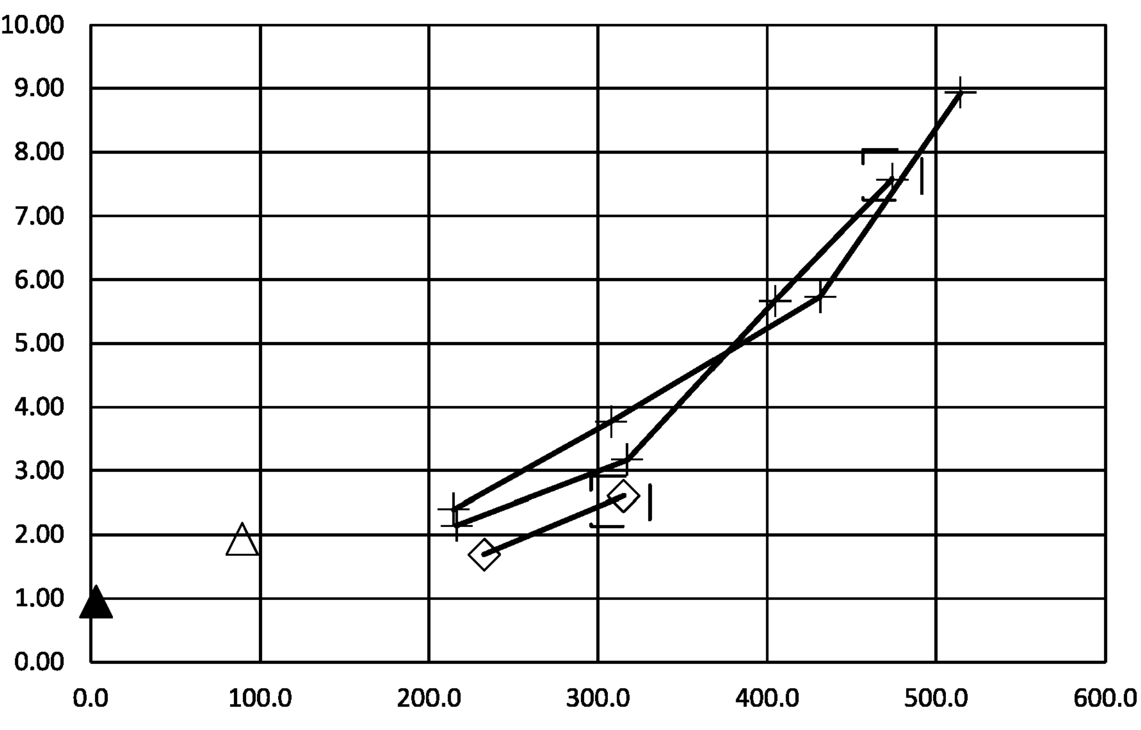

FIG. 5 illustrates part of the data previously explained for FIGS. 1 to 4 in a diagram in which the linear velocity in cm/s is plotted on the horizontal axis.

Again, in the form of vertical crosses, the data obtained according to the invention are illustrated with a tube diameter of 26 mm (graph starting at a value of about 2.2 on the vertical axis and ending at a value of about 7.5 on the vertical axis) and 20 mm (graph starting at a value of about 2.5 on the vertical axis and ending at a value of about 8.9 on the vertical axis). At the positions surrounded by dashed rectangles, there is an increased risk of thermal runaway.

FIG. 6 again illustrates the data shown in FIG. 5 in a diagram in which the specific catalyst loading per cooling surface in kg/m$^2$ is plotted on the horizontal axis.

Again, in the form of vertical crosses, the data obtained according to the invention are illustrated with a tube diameter of 26 mm (for higher values on the horizontal axis) and 20 mm (for lower values on the horizontal axis). At the positions surrounded by dashed rectangles, there is an increased risk of thermal runaway.

Figure 6:
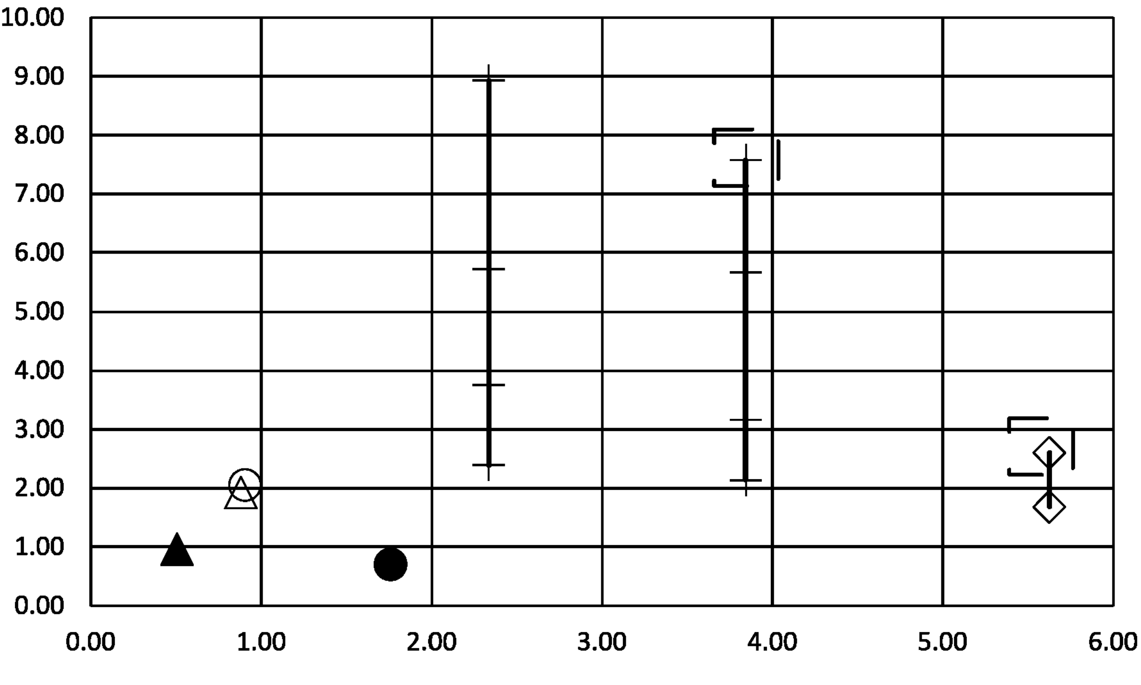
Figure 7:
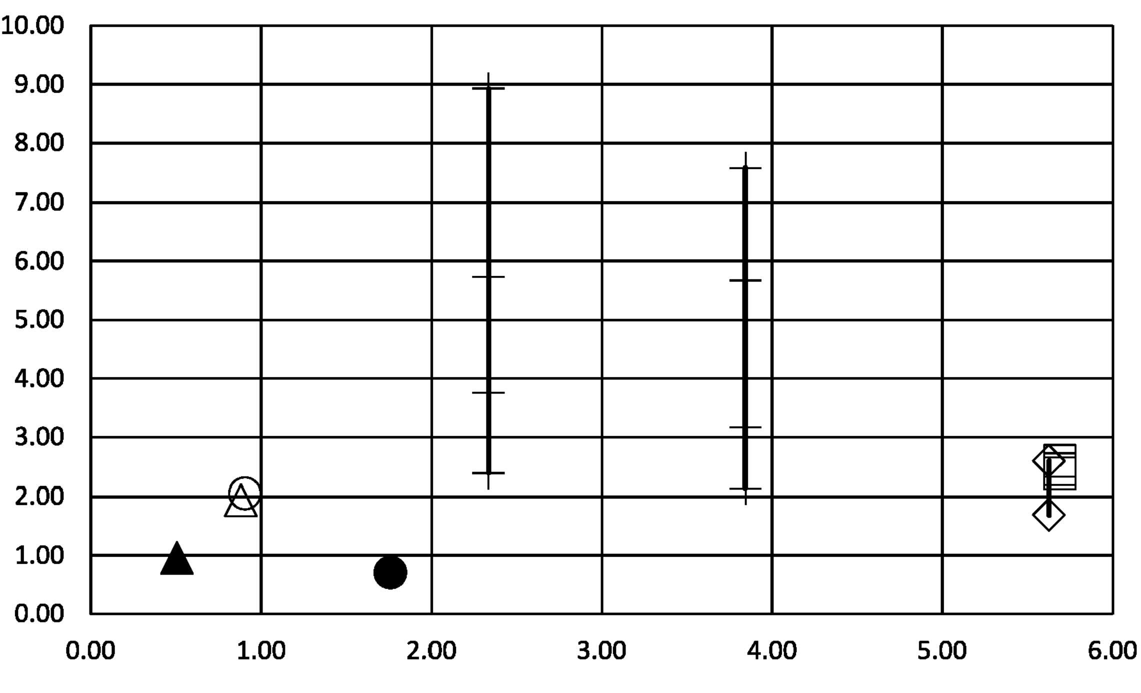

In FIG. 7, the data illustrated in FIG. 6 are supplemented by the data obtained from publication 3 (horizontal squares), with otherwise the same representation.

From the synopsis of FIGS. 5 and 6 in particular, it is evident that a strong process intensification can only be achieved for the middle range of the catalyst mass/cooling surface ratio claimed in accordance with the invention by increasing the linear velocity. FIG. 7 also shows that even for the conditions selected in accordance with publication 3 with a high specific catalyst loading per cooling surface, no potential for further increases in yield has been demonstrated.

What is particularly surprising is the fact that in designs according to the invention, no thermal runaway is to be expected even for very high specific ethylene yields. For all considerations with a reaction tube of 20 mm, an ethane conversion of more than 50% is always achieved, with a maximum temperature rise in the hotspot of less than 45 K compared to the salt outlet temperature. For a reaction tube of 26 mm, higher temperature rises generally result in the catalyst bed, which, starting from the point with the highest reactor load, can also lead to thermal runaway if the salt temperature is increased further.

It can thus be seen that only through suitable catalyst bed design, with moderate ratios of catalyst mass to cooling surface, can the potential of increasing linear velocity be fully exploited.

Figure 8:
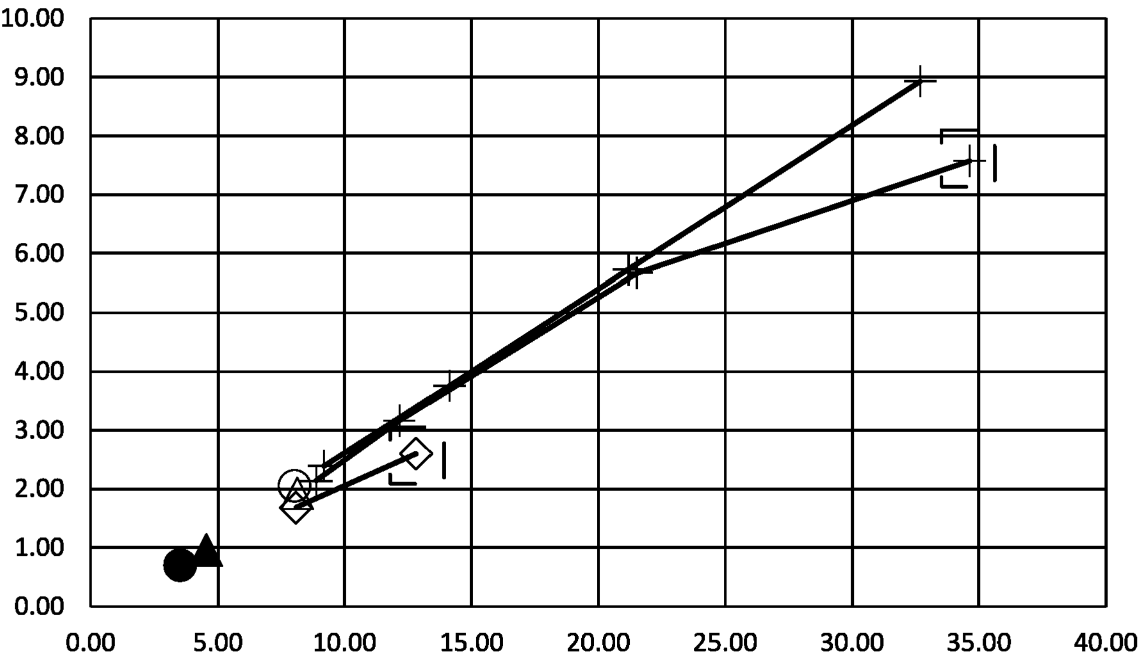
Figure 9:
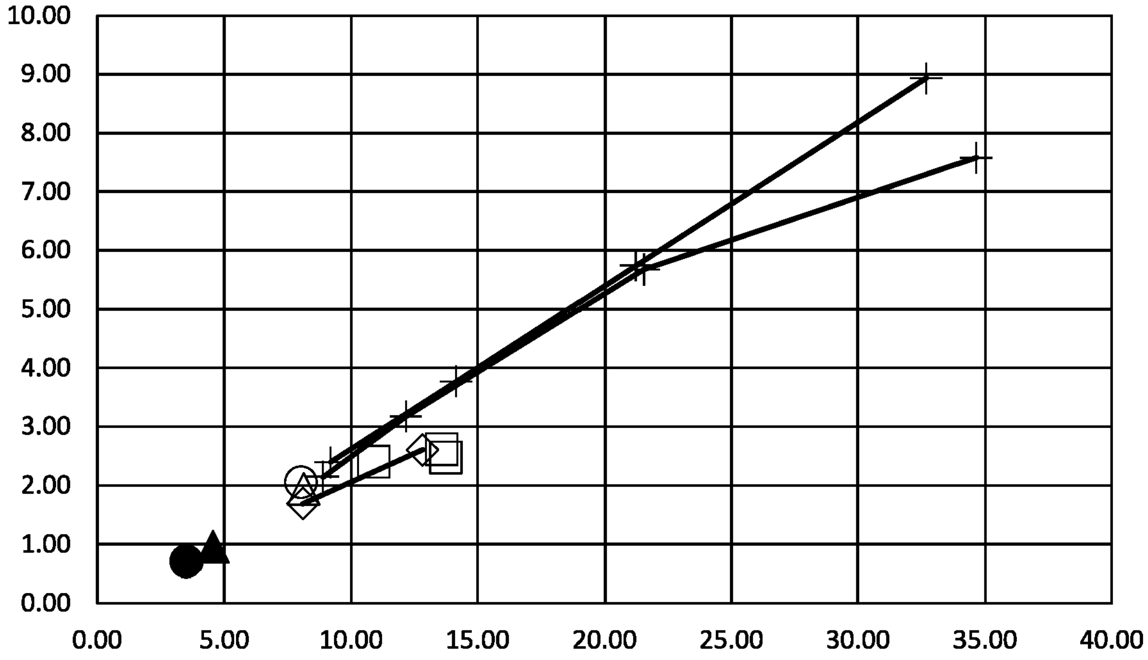

This can also be seen when looking at FIGS. 8 and 9, which, in the case of FIG. 8 compared to FIG. 2, are supplemented by the data obtained according to the invention (crosses, upper data points correspond in each case to the tube diameter 20 mm) and, in the case of FIG. 9, additionally by the data according to publication 3. For these designs, an almost linear increase of the specific ethylene yield with increasing load can be achieved up to very high ranges. This is in particular in contrast to the described rather flat increase for the single-layer bed with high catalyst mass to cooling surface ratio.

Tables 1A and 1B each show a comparison of reactor data in terms of reaction parameters and product performance for a standard design case (base case) and several comparison cases at high linear velocity for a tube diameter of 20 mm (Table 1A) and 26 mm (Table 1B). The catalyst used was a MoVNbTe-based mixed oxide loaded into the reactor on a support in the form of rings. The catalyst bed has a length of 6.6 m (26 mm tube) and 4.6 m (20 mm tube), respectively, being poured in three layers of different activity, with activity increasing in the flow direction. The length of the differently active zones, the catalyst particle geometry and the activity gradation are identical for cases with the same tube diameter. Upstream of the catalyst bed is a bed of inert material (length 1.4 m, also rings of the same size), which serves as a preheating zone.

As previously mentioned, it is possible according to the invention that for reaction tubes with multilayer or multiple catalyst beds, the ratios of active catalyst mass to effective cooling surface calculated separately for individual layers or catalyst beds lie outside the range provided for the average ratio of active catalyst mass to effective cooling surface for the reaction tube in a corresponding embodiment of the invention. This also applies, for example, to the reactor tube designs given here as examples:

In the case of the 20 mm diameter tube, the average ratio of active catalyst mass to effective cooling surface over the three catalyst beds is 2.33 (see Table 1A), while the catalyst beds arranged along the direction of flow have ratios of 0.91, 1.83 and 4.11, respectively. Thus, the ratio for the first catalyst bed here is below the value of 1.5.

In the case of the 26 mm diameter tube, the average ratio of active catalyst mass to effective cooling surface over the three catalyst beds is 3.84 (see Table 1B), while the catalyst beds arranged along the direction of flow have ratios of 2.44, 3.74 and 5.35, respectively. Thus, the ratio for the last catalyst bed is above the value of 5 here.

TABLE 1A

Reactor diameter 20 mm, reactor length 6 m, total height of active layers 4.6 m, total length-to-diameter ratio 230, active catalyst mass 0.675 kg.

| | | | | |
|---|---|---|---|---|
| Operating pressure [bara] | 3.6 | 4 | 4.5 | 6.1 |
| Coolant temperature [° C.] | 370 | 380 | 390 | 405 |
| WHSV [kg feed/(h * kg cat)] | 3.9 | 6.1 | 9.1 | 14.0 |
| Linear velocity [cm/s] | 214.2 | 307.6 | 431.4 | 514.4 |
| Relative molar ethylene yield with respect to ethane feed at reactor inlet | 43.2% | 44.1% | 44.8% | 45.3% |
| Ethylene production per individual tube [kg/h]. | 0.69 | 1.09 | 1.66 | 2.58 |
| No. of tubes required in shell-and-tube reactor for 250 kta ethylene annual production | 43345 | 27585 | 18099 | 11625 |
| Cooling surface per single tube [m$^2$] | 0.289 | 0.289 | 0.289 | 0.289 |
| Total cooling surface in shell-and-tube reactor [m$^2$]. | 12528 | 7973 | 5231 | 3360 |
| Specific ethylene yield per cooling surface [kg/(h * m$^2$)] | 2.39 | 3.76 | 5.74 | 8.93 |
| Specific catalyst loading per cooling surface [kg/m$^2$]. | 2.33 | 2.33 | 2.33 | 2.33 |
| Load with insert per cooling surface [kg/(h * m$^2$)] | 9.19 | 14.14 | 21.20 | 32.69 |

TABLE 1B

Reactor diameter 26 mm, reactor length 8.05 m, total height of active layers 6.6 m, total length-to-diameter ratio 254, active catalyst mass 2.07 kg.

| | | | | |
|---|---|---|---|---|
| Operating pressure [bara] | 3.5 | 3.5 | 5 | 7 |
| Coolant temperature [° C.] | 327 | 350 | 355 | 350 |
| WHSV [kg use/(h * kg cat)] | 2.3 | 3.2 | 5.6 | 9.0 |
| Linear velocity [cm/s] | 216.2 | 317.2 | 404.4 | 474.0 |
| Relative molar ethylene yield based on ethane feed at reactor inlet | 40.6% | 44.0% | 44.5% | 36.9% |
| Ethylene production per individual tube [kg/h]. | 1.15 | 1.71 | 3.06 | 4.09 |
| No. of tubes required in shell-and-tube reactor for 250 kta ethylene annual production | 25997 | 17560 | 9814 | 7344 |

TABLE 1B-continued

| Reactor diameter 26 mm, reactor length 8.05 m, total height of active layers 6.6 m, total length-to-diameter ratio 254, active catalyst mass 2.07 kg. | | | | |
|---|---|---|---|---|
| Cooling surface per single tube [$m^2$] | 0.539 | 0.539 | 0.539 | 0.539 |
| Total cooling surface in shell-and-tube reactor [$m^2$]. | 14015 | 9467 | 5291 | 3959 |
| Specific ethylene yield per cooling surface [kg/(h * $m^2$)] | 2.14 | 3.17 | 5.67 | 7.58 |
| Specific catalyst loading per cooling surface [kg/$m^2$]. | 3.84 | 3.84 | 3.84 | 3.84 |
| Load with insert per cooling surface [kg/(h * $m^2$)] | 8.89 | 12.17 | 21.53 | 34.64 |

Figure 10:
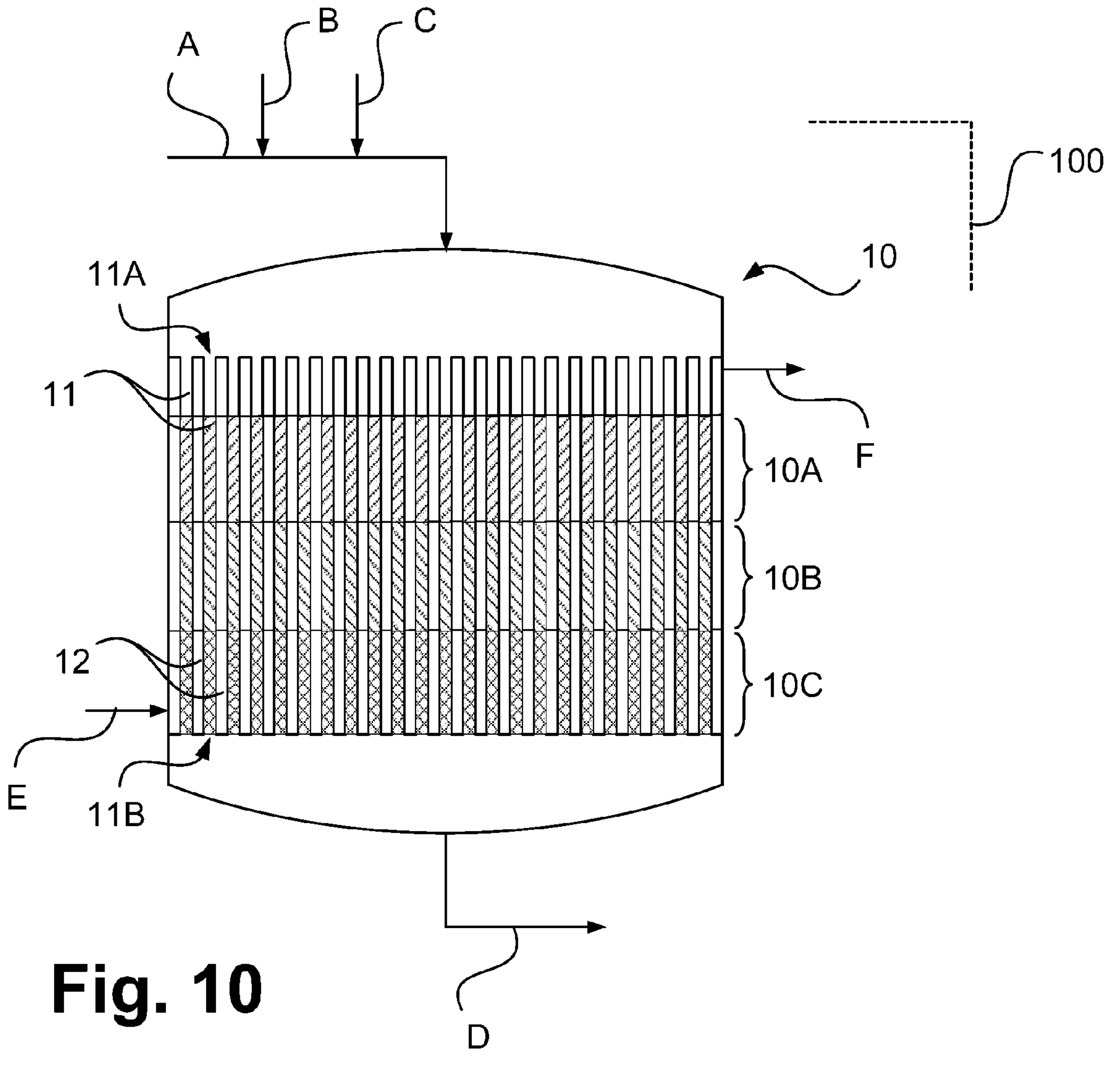
FIG. 10 illustrates a plant for the production of ethylene by oxidative dehydrogenation of ethane according to one embodiment of the invention.

FIG. 10 illustrates a plant for the production of ethylene by oxidative dehydrogenation of ethane according to one embodiment of the invention in the form of a highly simplified plant diagram and is designated 100. The entire plant is shown only schematically.

The system 100 has a shell-and-tube reactor 10 with multiple and only partially designated reaction tubes 11, to which an ethane-containing gas mixture obtained in any manner is fed in the form of a material stream A. The material stream A can be taken from a rectification unit, which is not shown. The material stream A can be taken, for example, from a rectification unit not shown, which separates higher hydrocarbons from a starting mixture. The stock stream A may also be preheated and processed in other ways, for example. The material stream A may already contain oxygen and, if necessary, a diluent such as steam; however, corresponding media may also be added upstream of or in the shell-and-tube reactor 10, as illustrated here by way of example in the form of material streams B and C.

The reaction tubes 11 run through several, in the example shown three, reaction zones 10A, 10B, 10C and are surrounded by a jacket area 12. Catalyst beds are provided in each of the reaction tubes 11 in the corresponding reaction zones 10A, 10B, 10C and are illustrated in the form of different hatchings. A gas mixture containing ethane as well as oxygen and possibly a diluent is passed through the reaction zones 10A to 10C one after the other in the form of the material stream A or the combined material streams A to C, respectively. The reaction zones 10A to 10C are preceded by an inert zone which is not separately designated. The reaction tubes 11 extend between a first end 11A and a second end 11B (designated only in the case of a reaction tube) and the reaction zones 10A to 10C are arranged between these ends 11A, 11B.

The reaction zones 10A, 10B, 10C are characterized in particular by different catalyst activities in the catalyst beds, as previously explained in detail. Non-inventive embodiments, can also be realized without a corresponding formation of different reaction zones 10A, 10B, 10C or catalyst beds. Alternatively or additionally, a zonally different or uniform temperature control may be implemented.

A process gas flows from the shell-and-tube reactor 10 in the form of a process gas stream D containing ethylene formed in the shell-and-tube reactor 10 by reacting a portion of the ethane by oxidative dehydrogenation. Further, the process gas contains acetic acid, which is also formed from ethane in the shell-and-tube reactor 10, as well as water, carbon monoxide, carbon dioxide, unreacted oxygen, and the diluent(s) and other compounds if added or previously formed in the shell-and-tube reactor 10. The reaction tubes 11 are tempered by means of a flow of tempering agent E through the shell region which is carried out in the form of an effluent F from the shell region. As not illustrated here, in particular several temperature control medium circuits can be provided here, which temperature control or cool the reaction tubes 11 in sections. A wall of the reaction tubes 11 in the region of the respective catalyst beds defines an active cooling surface for the catalyst beds in each case.

It is understood that the plant 100 may comprise one, as illustrated, but also several, for example parallel operated, shell-and-tube reactors 10. In the latter case, these shell-and-tube reactors 10 are each supplied with corresponding reaction feeds, which may have the same or different compositions, and corresponding process gas streams D are formed in each case. The latter can be combined and supplied together as process gas to subsequent process steps or plant sections.

Downstream of the shell-and-tube reactor 10, a water partial pressure can be detected. This can be adjusted, for example, by adding water or steam to the gas mixture of the material stream A or in the form of the material streams B or C. The water partial pressure can also be adjusted. A further influence, in particular a fine adjustment, can be made by adjusting the temperature in the shell-and-tube reactor 10.

Subsequent process steps or plant components are not illustrated. In these, the process gas can be brought into contact with wash water or a suitable aqueous solution, whereby the process gas can be cooled in particular and acetic acid can be washed out of the process gas. The process gas at least largely freed from acetic acid can be further treated and subjected to ethylene separation. Ethane contained in the process gas can be recycled to the reactor 10.

The invention claimed is:

1. A method for producing ethylene by oxidative dehydrogenation of ethane, comprising:

providing a shell-and-tube reactor having reaction tubes extending between a first end and a second end, wherein a plurality of catalyst beds are disposed in each of said reaction tubes, and in each of said reaction tubes, a ratio of a total length of the plurality of catalyst beds between said first end and said second end to a diameter of each of said reaction tubes has a value between 150 and 400; and feeding a feed comprising ethane and oxygen to the shell-and-tube reactor operating under oxidative dehydrogenation conditions;

wherein:

the shell-and-tube reactor is operated at a linear velocity of 250 to 800 cm/s;

the plurality of catalyst beds are configured such that the plurality of catalyst beds in each of the reaction tubes have a different catalyst activity;

an average ratio of active catalyst mass to effective cooling surface for the plurality of catalyst beds in each of the reaction tubes is in a range between 1.5 and 5 kg/$m^2$, wherein in at least one of the catalyst beds in each of the reaction tubes considered individually, a ratio of active catalyst mass to effective cooling surface is in the range between 1.5 and 5 kg/$m^2$; and the average ratio of the active catalyst mass to the effective cooling surface for the plurality of catalyst beds in each of the reaction tubes is a quotient between a sum of the active catalyst masses in all of the respective catalyst beds and the sum of all inner surfaces of the reaction tube surrounding these catalyst beds, respectively.

2. The method according to claim 1, wherein the shell-and-tube reactor is operated at a weight hourly space velocity of greater than 3 kg and less than 20 kg feed per hour per kg of catalyst.

3. The method according to claim 1, wherein the shell-and-tube reactor is operated at a linear velocity greater than 300 cm/s.

4. The method according to claim 3, wherein the shell-and-tube reactor is operated such that a maximum temperature in the plurality of catalyst beds is less than 500° C.

5. The method according to claim 4, wherein a packing selected from rings, pellets, extrudates, or combinations thereof is used in the plurality of catalyst beds.

6. The method according to claim 5, in which a water feed is metered into the shell-and-tube reactor as a function of a detected catalyst activity in the shell-and-tube reactor.

7. The method according to claim 6, in which one or more cooling media flow through the shell-and-tube reactor.

8. The method according to claim 7, wherein different regions of the shell-and-tube reactor are cooled to different extents.

9. The method according claim 3, wherein a packing selected from rings, pellets, extrudates, or combinations thereof is used in the plurality of catalyst beds.

10. The method according to claim 3, in which a water feed is metered into the shell-and-tube reactor as a function of a detected catalyst activity in the shell-and-tube reactor.

11. The method according to claim 3, in which one or more cooling media flow through the shell-and-tube reactor.

12. The method according to claim 11, wherein different regions of the shell-and-tube reactor are cooled to different extents.

13. The method according to claim 1, wherein the shell-and-tube reactor is operated such that a maximum temperature in the plurality of catalyst beds is less than 500° C.

14. The method according claim 1, wherein a packing selected from rings, pellets, extrudates, or combinations thereof is used in the plurality of catalyst beds.

15. The method according to claim 1, in which a water feed is metered into the shell-and-tube reactor as a function of a detected catalyst activity in the shell-and-tube reactor.

16. The method according to claim 1, in which one or more cooling media flow through the shell-and-tube reactor.

17. The method according to claim 16, wherein different regions of the shell-and-tube reactor are cooled to different extents.

18. The method according to claim 1, wherein different regions of the shell-and-tube reactor are cooled to different extents.

19. A plant for producing ethylene by oxidative dehydrogenation of ethane, comprising;

a shell-and-tube reactor having reaction tubes extending between a first end and a second end, wherein:
- a plurality of catalyst beds are disposed in each of the reaction tubes; and
- in each of the reaction tubes, a ratio of a total length of the plurality of catalyst beds between the first end and the second end to a diameter of each of the reaction tubes has a value between 150 and 400; and a feed source configured to provide a feed comprising ethane and oxygen to the shell-and-tube reactor;

wherein:

the shell-and-tube reactor is configured to operate at a linear velocity of 250 to 800 cm/s;
- the plurality of catalyst beds are configured such that the plurality of catalyst beds in each of the reaction tubes have a different catalyst activity; and
- an average ratio of active catalyst mass to effective cooling area for the plurality of catalyst beds in each of the reaction tubes is in a range between 1.5 and 5 $kg/m^2$, wherein in at least one of the catalyst beds in each of the reaction tubes considered individually, a ratio of active catalyst mass to effective cooling surface is in the range between 1.5 and 5 $kg/m^2$, and
- the average ratio of the active catalyst mass to the effective cooling surface for the plurality of catalyst beds in each of the reaction tubes is a quotient between a sum of the active catalyst masses in all of the respective catalyst beds and the sum of all inner surfaces of the reaction tube surrounding these catalyst beds, respectively.

* * * * *